US010439408B1

(12) United States Patent
Bastiyali

(10) Patent No.: US 10,439,408 B1
(45) Date of Patent: Oct. 8, 2019

(54) MODULAR CELL PHONE STORAGE LOCKER

(71) Applicant: Tarkan Bastiyali, New York, NY (US)

(72) Inventor: Tarkan Bastiyali, New York, NY (US)

( * ) Notice: Subject to any disclaimer, the term of this patent is extended or adjusted under 35 U.S.C. 154(b) by 37 days.

(21) Appl. No.: 15/925,847

(22) Filed: Mar. 20, 2018

(51) Int. Cl.
    *H02J 7/00*     (2006.01)
    *A61L 2/24*     (2006.01)
    *A61L 2/10*     (2006.01)
    *A47B 81/00*     (2006.01)

(52) U.S. Cl.
    CPC ............ *H02J 7/0027* (2013.01); *A47B 81/00* (2013.01); *A61L 2/10* (2013.01); *A61L 2/24* (2013.01); *H02J 7/0044* (2013.01)

(58) Field of Classification Search
    CPC ........ H02J 7/0027; H02J 7/0044; A47B 81/00
    USPC .................... 320/107, 114, 115, 155
    See application file for complete search history.

(56) References Cited

U.S. PATENT DOCUMENTS

| | | | |
|---|---|---|---|
| 5,744,933 A * | 4/1998 | Inoue ................... | G06Q 20/127 320/110 |
| 8,699,235 B2 | 4/2014 | Soufan | |
| 9,680,317 B2 | 6/2017 | Roberts | |
| 9,756,552 B1 | 9/2017 | Pickover | |
| 2005/0104555 A1 * | 5/2005 | Simmonds-Short ........................ | H02J 7/0027 320/107 |
| 2006/0229112 A1 | 10/2006 | Forro | |
| 2008/0132278 A1 | 6/2008 | Dovey | |
| 2009/0026899 A1 * | 1/2009 | Jerro ..................... | A47B 81/00 312/223.4 |
| 2015/0008868 A1 | 1/2015 | Whitehead | |
| 2015/0137738 A1 | 5/2015 | Chien | |
| 2017/0096279 A1 * | 4/2017 | Campalans ............. | H04L 67/42 |

* cited by examiner

*Primary Examiner* — Edward Tso
*Assistant Examiner* — Aaron Piggush

(57) ABSTRACT

The modular cell phone storage locker may comprise a cabinet with one or more doors. The interior space of the cabin may comprise one or more internal compartments defined by the exterior walls of the cabinet and internal dividers. A charging port and a disinfecting device may be located within each compartment. The doors may be prevented from opening by a lock, which is responsive to a timer. Locked periods and unlocked periods may be defined through a keypad on an operator panel. While locked, cell phones left in a compartment may be recharged and disinfected. A software application on the phone may prevent usage of the phone and modify phone operation during locked periods. One or more time displays visible on the exterior of the cabinet may display information pertinent to the operation of the timer. A fingerprint reader may allow administrator access to the lock.

18 Claims, 4 Drawing Sheets

MODULAR CELL PHONE STORAGE LOCKER

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the fields of cell phones and storage containers, more specifically, a modular cell phone storage locker.

In some situations it may be desirable to have the owners of cell phones placed their phones into a secure storage locker such that the owners may not use or access their phones for specific periods of time. Non-limiting examples of where such situations may be found include classrooms, military barracks, theaters, and restaurants. While the phones are in the secure storage locker, there is an opportunity to recharge the phones and disinfect the outside surfaces of the phones.

SUMMARY OF INVENTION

The modular cell phone storage locker may comprise a cabinet with one or more doors. The interior space of the cabin may comprise one or more internal compartments defined by the exterior walls of the cabinet and internal dividers. A charging port and a disinfecting device may be located within each compartment. The doors may be prevented from opening by a lock which is responsive to a timer. Locked periods and unlocked periods may be defined through a keypad on an operator panel. While locked, cell phones left in a compartment may be recharged and disinfected. A software application on the phone may prevent usage of the phone and modify phone operation during locked periods. One or more time displays visible on the exterior of the cabinet may display information pertinent to the operation of the timer. A fingerprint reader may allow administrator access to the lock.

An object of the invention is to secure cell phones within a locked cabinet during periods of time when the phones should not be used.

Another object of the invention is to recharge the cell phones while they are secured.

A further object of the invention is to disinfect the outside surface of the cell phones while they are secured.

Yet another object of the invention is to display timing information pertinent to the operation of the timed lock.

A further object of the invention is to construct the cabinet with materials that enable the overall device to be soundproof.

A further object of the invention is to construct the cabinet with materials that enable the overall device to be fireproof for an undefined amount of time.

A further object of the invention is to include a pager that works to alert an end user that the cabinet housing a smart phone has been sealed therein for a designated amount of time, which has elapsed and that the end user may retrieve the smart phone.

These together with additional objects, features and advantages of the modular cell phone storage locker will be readily apparent to those of ordinary skill in the art upon reading the following detailed description of the presently preferred, but nonetheless illustrative, embodiments when taken in conjunction with the accompanying drawings.

In this respect, before explaining the current embodiments of the modular cell phone storage locker in detail, it is to be understood that the modular cell phone storage locker is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the modular cell phone storage locker.

It is therefore important that the claims be regarded as including such equivalent construction insofar as they do not depart from the spirit and scope of the modular cell phone storage locker. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description. As used herein, the word "or" is intended to be inclusive.

Figure 1:
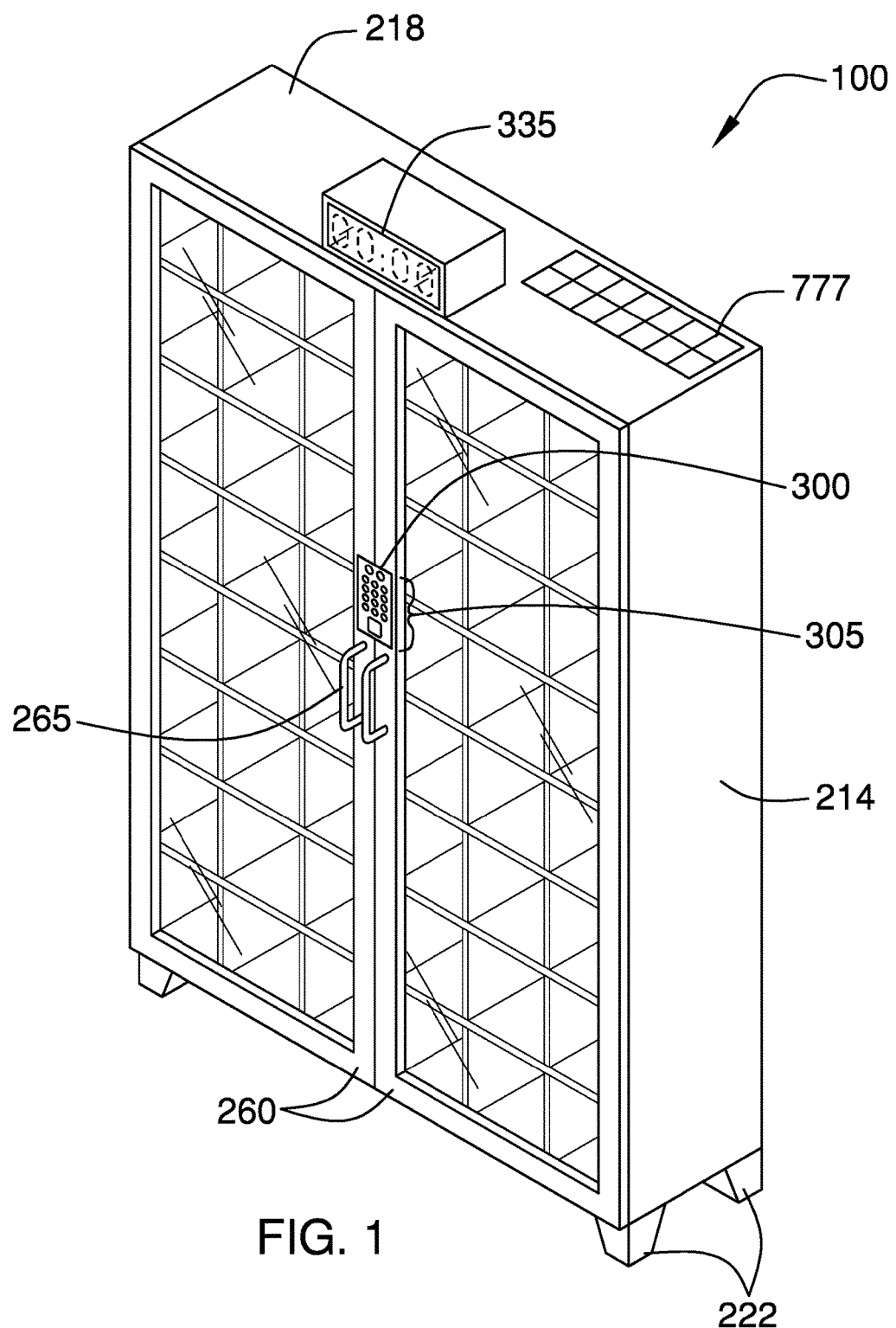
FIG. 1 is a perspective view of an embodiment of the disclosure with the doors in the closed position.
Figure 2:
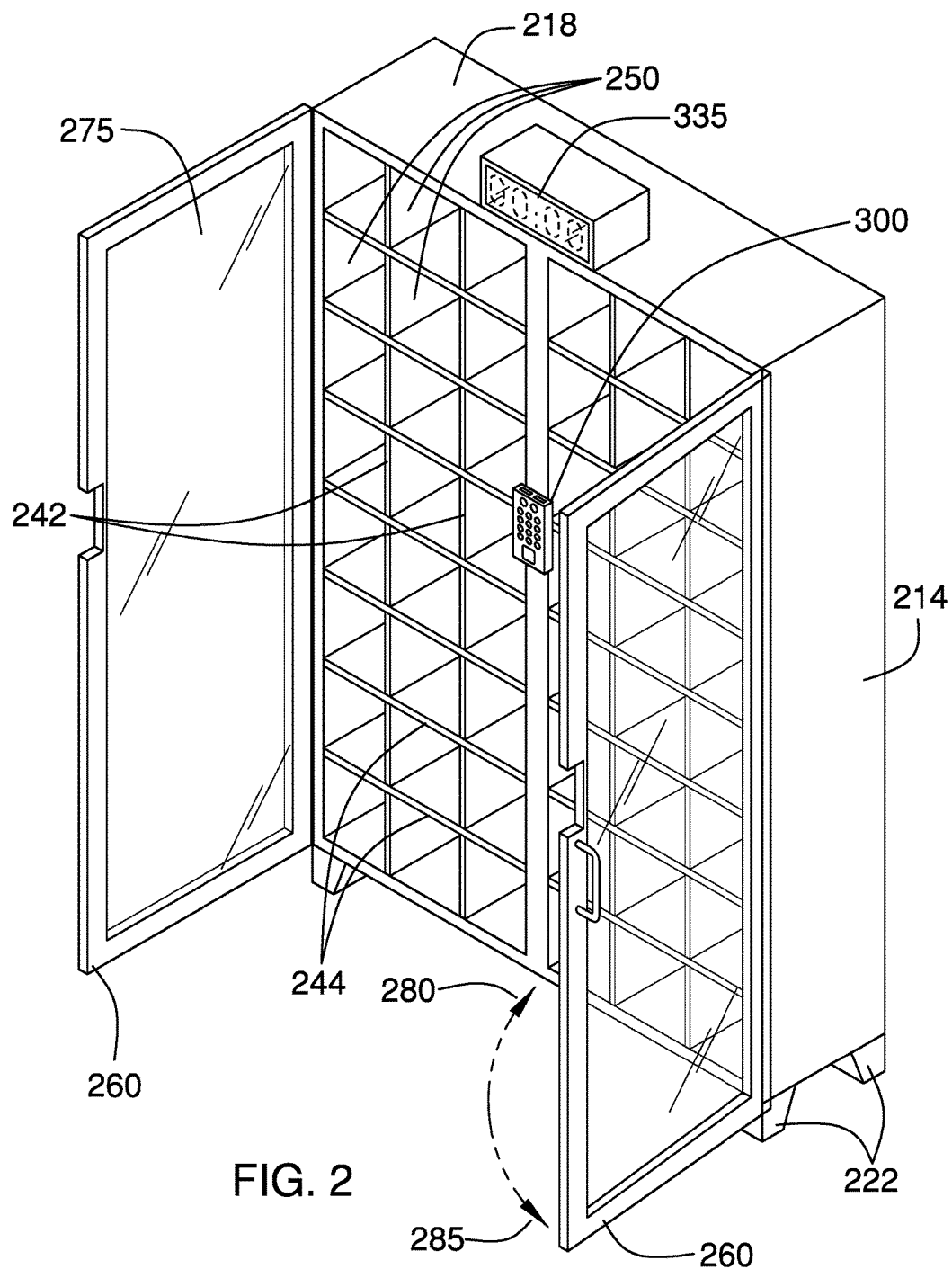
FIG. 2 is a perspective view of an embodiment of the disclosure with the doors in the open position.
Figure 3:
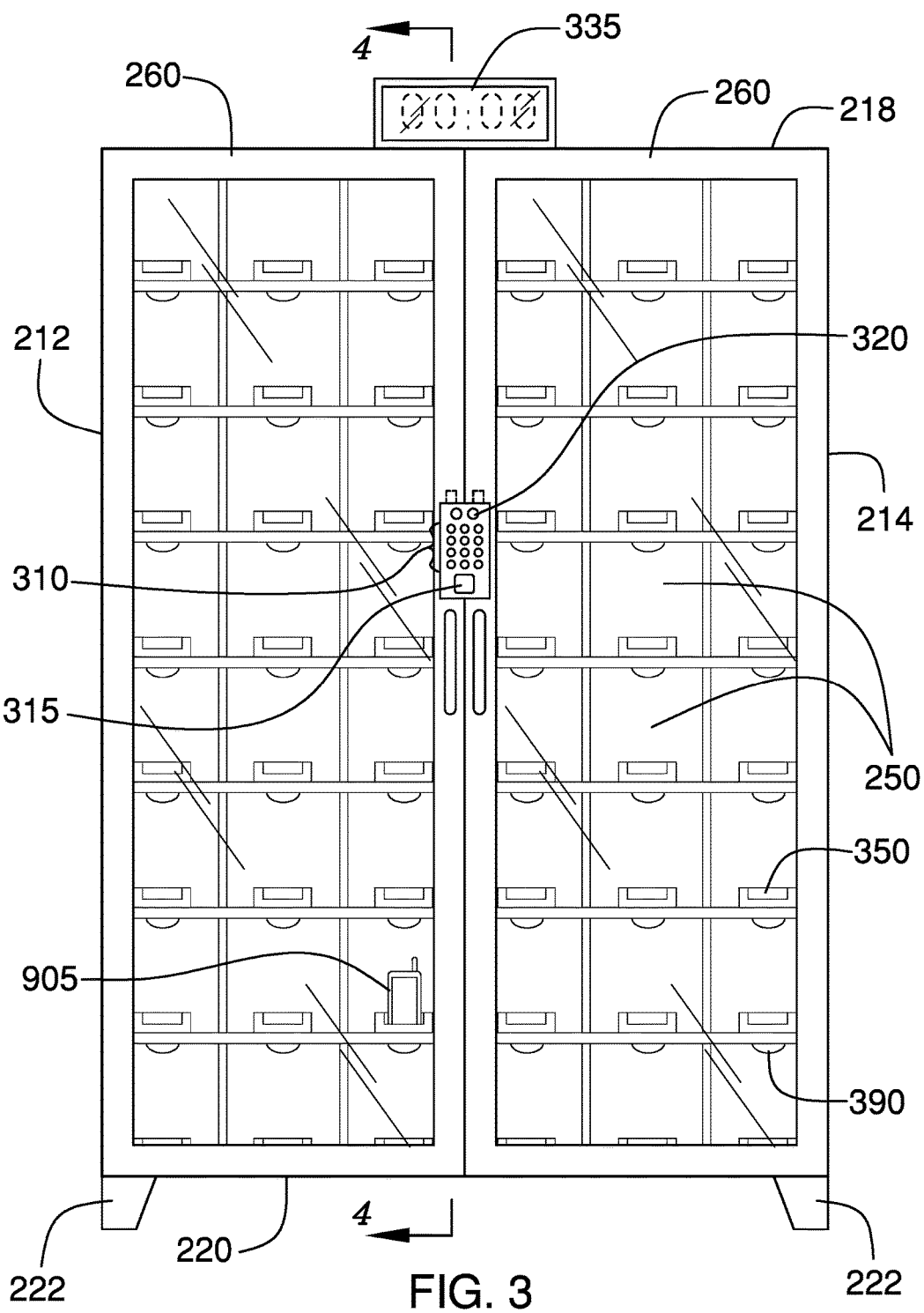
FIG. 3 is a front view of an embodiment of the disclosure.
Figure 4:
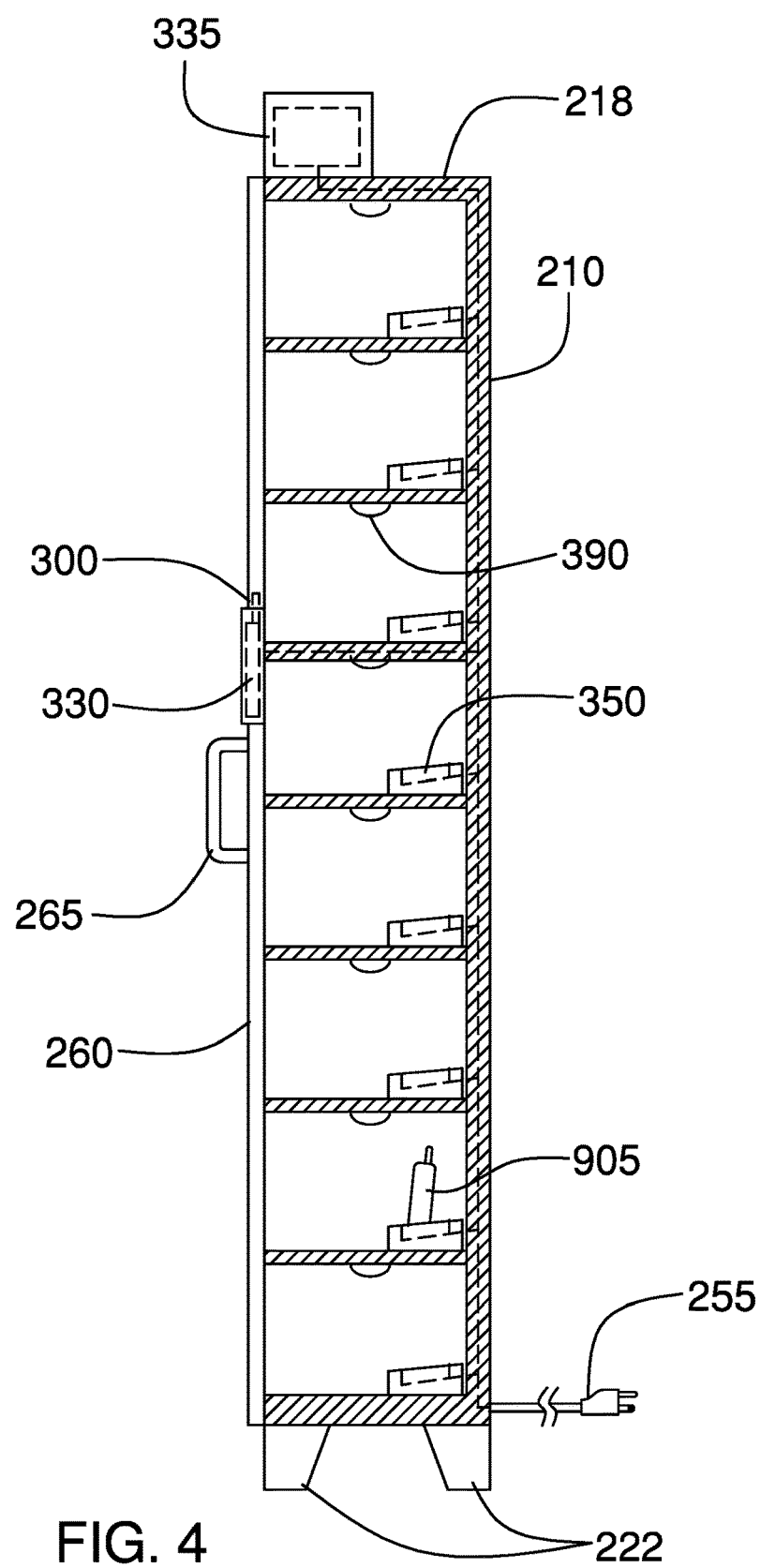
FIG. 4 is a cross-sectional view of an embodiment of the disclosure across 4-4 as shown in FIG. 3.

Detailed reference will now be made to a first potential embodiment of the disclosure, which is illustrated in FIGS. 1 through 4.

The modular cell phone storage locker 100 (hereinafter invention) comprises a cabinet, one or more doors 260, one or more internal compartments 250, a lock 300, and a timer 330. The invention 100 may provide a container where one or more cell phones may be secured to prevent use of the one or more cell phones except during one or more predefined time periods.

The cabinet comprises a rear wall 210, a left wall 212, a right wall 214, a top 218, and a bottom 220. The cabinet may be an enclosure for the invention 100. The left edge of the rear wall 210 may be coupled to the rear edge of the left wall 212. The right edge of the rear wall 210 may be coupled to the rear edge of the right wall 214. The top edge of the rear wall 210 may be coupled to the rear edge of the top 218. The bottom edge of the rear wall 210 may be coupled to the rear edge of the bottom 220. The top edge of the left wall 212 may be coupled to the left edge of the top 218. The bottom edge of the left wall 212 may be coupled to the left edge of the bottom 220. The top edge of the right wall 214 may be coupled to the right edge of the top 218. The bottom edge of the right wall 214 may be coupled to the right edge of the bottom 220.

The cabinet may comprise a plurality of feet 222 on the outside of the bottom 220 of the cabinet and/or one or more mounting holes (not illustrated in the figures) on the rear wall 210 for hanging the cabinet on a wall of a building (not illustrated in the figures).

The one or more doors 260 may be front covers for the cabinet. Each of the one or more doors 260 may be hingedly coupled to the cabinet via one or more door hinges (not illustrated in the figures). The one or more doors 260 may be locked in a closed position 280 to prevent access to the contents of the cabinet. The one or more doors 260 may be moved to an open position 285 when not locked to provide access to the contents of the cabinet. Each of the one or more doors 260 may comprise a handle 265.

In some embodiments, each of the one or more doors 260 may comprise one or more viewing panes 275 which may be transparent or translucent. The one or more viewing panes 275 may allow viewing of the contents of the cabinet. In some embodiments, the one or more viewing panes 275 may be UV opaque.

The cabinet may comprise one or more internal dividers. The rear wall 210, the left wall 212, the right wall 214, the top 218, the bottom 220, and the one or more doors 260 may comprise a grouping of walls referred to as external walls. The external walls, the one or more internal dividers, or combinations thereof may define the one or more internal compartments 250. Each of the one or more internal compartments 250 may be a storage location for an individual cell phone 905.

The one or more internal dividers may comprise one or more internal horizontal dividers 244. The one or more internal horizontal dividers 244 may be horizontal planes dividing the interior of the cabinet into two or more distinct, vertically-aligned spaces. The one or more internal horizontal dividers 244 may be coupled at their rear edge to the rear wall 210, on their left edge to the left wall 212, and at their right edge to the right wall 214. In some embodiments, the two or more distinct, vertically-aligned spaces may be of equal width.

The one or more internal dividers may comprise one or more internal vertical dividers 242. The one or more internal vertical dividers 242 may be vertical planes dividing the interior of the cabinet into two or more distinct, horizontally-aligned spaces. The one or more internal vertical dividers 242 may be coupled at their rear edge to the rear wall 210, on their top edge to the top 218, and at their bottom edge to the bottom 220. In some embodiments, the two or more distinct, horizontally-aligned spaces may be of equal height.

The one or more internal compartments 250 may be organized into rows where each of the one or more internal compartments 250 in a row is the same height above the bottom 220, into columns where each of the one or more internal compartments 250 in a column is the same distance from the left wall 212, or into a matrix of rows and columns. The smallest possible cabinet may comprise a single one of the one or more internal compartments 250 using only the external walls and none of the one or more internal dividers. FIGS. 1 through 4 illustrate embodiments that provide forty eight of the one or more internal compartments 250 organized into eight rows and 6 columns.

The lock 300 may be a device that prevents the one or more doors 260 from opening when locked and allows the one or more doors 260 to open when unlocked. The lock 300 may prevent opening when locked by creating an electromechanical linkage between the one or more doors 260, the cabinet, the one or more internal dividers, or combinations thereof. The lock 300 may allow opening by breaking the electromechanical linkage.

The lock 300 may comprise an operator panel 305. The operator panel 305 may comprise a key pad 310. The operator panel 305 may be adapted to allow a cabinet administrator (not illustrated in the figures) to control the operation of the lock 300 by interacting with the key pad 310. As non-limiting example, the cabinet administrator may use the operator panel 305 to enter or change combinations, set the timer 330, override the timer 330 to force locking or unlocking, or train a fingerprint reader 315.

The operator panel 305 may comprise one or more indicators 320. The one or more indicators 320 may express an operational state of the operator panel 305, the lock 300, the timer 330, or combinations thereof. As non-limiting examples, the one or more indicators 320 may express that the lock 300 is locked or unlocked, that the timer 330 has been programmed, or that a fingerprint has been recognized by the fingerprint reader 315. Optionally, the one or more indicators 320 may involve colored lights, such as red or green to indicate that the invention 100 is locked or unlocked, respectively.

The operator panel 305 may comprise the fingerprint reader 315. The fingerprint reader 315 may be adapted to allow the cabinet administrator to use a fingerprint to identify themselves to the lock 300. As non-limiting examples, once the cabinet administrator has been identified via the fingerprint reader 315, the lock 300 may allow use of an additional set of functions, such as allowing the state of the lock 300 to be overridden, allowing keypad codes to be changed, or allowing the one or more predefined time periods for the timer 330 to be programmed.

The lock 300 may comprise the timer 330. The timer 330 may establish the temporal boundaries of the one or more predefined time periods during which the one or more cell phones may or may not be accessed. During a locked period, the timer 330 may cause the lock 300 to activate and prevent the one or more doors 260 from opening. During an unlocked period, the timer 330 may allow the lock 300 to deactivate the lock 300 and allow the one or more doors 260 to be opened. The one or more predefined time periods may be defined using the key pad 310 on the operator panel 305.

In some embodiments, the invention 100 may comprise one or more time displays 335. The one or more time displays 335 may be mounted where they are visible from a position outside of the cabinet. The one or more time displays 335 may operate under the control of the timer 330 and may display time values pertinent to the operation of the timer 330. As non-limiting examples, the one or more time displays 335 may display any or all of the current time, the time remaining until the lock 300 is activated, the time remaining until the lock 300 is deactivated, and/or the amount of time that the lock 300 has been activated.

In some embodiments, the lock 300 may connect wirelessly to a software application (not illustrated in the figures) installed on each of the individual cell phones 905 that may be placed inside of the cabinet. The software application on each of the individual cell phones 905 may disable or modify features of the individual cell phones 905. As non-limiting examples, the software application may prevent usage of the individual cell phone 905 if it is removed from the cabinet, may provide an automatic response to incoming text messages or calls received during the one or more predefined time periods when the individual cell phone 905 is locked, or may place the individual cell phone 905 into a reduced power mode of operation.

The invention 100 may further comprise a charging port 350 located within each of the one or more internal compartments 250. The charging port 350 may recharge the individual cell phone 905 while the individual cell phone 905 resides inside of one of the one or more internal compartments 250. The charging port 350 may comprise one or more power cables, one or more docking stations, or a combination thereof. The charging port 350 may be powered by AC power distributed within the cabinet to each of the one or more internal compartments 250 from an AC power cord 255, by DC power distributed within the cabinet to each of the one or more internal compartments 250 from a DC power supply (not illustrated in the figures), or by a combination thereof.

It shall be noted that the invention 100 may include a solar panel 777, which would generate electricity that the invention 100 could use in lieu of or in combination with the power cord 255. The solar panel 777 may be provided on the top 218 of the cabinet. Alternatively, the solar panel 777 may be detached from or provided on another surface of the invention 100.

The invention 100 may further comprise a disinfecting device 390 located within each of the one or more internal compartments 250. The disinfecting device 390 may be a device that destroys bacteria on the surface of the individual cell phone 905. As a non-limiting example, the disinfecting device 390 may be an ultraviolet (UV) light that is illuminated while the individual cell phone 905 is within one of the one or more internal compartments 250.

In use, the invention 100 is installed in a public area of a venue. As non-limiting examples, a venue may be a school building, a military installation, a gymnasium, a restaurant, a sporting arena, a hospital, a theater, an office complex, a funeral home, or a personal residence. The cabinet administrator may use the key pad 310 on the operator panel 305 to establish the one or more predefined time periods during which the cabinet will be locked. The cabinet administrator may unlock the lock 300, move the one or more doors 260 to the open position 285, and allow cell phone owners (not illustrated in the figures) to place their phones into the cabinet. Each the cell phone owner may place the individual cell phone 905 into one of the one or more internal compartments 250 and couple the individual cell phone 905 to the charging port 350. The one or more doors 260 may be closed and at a programmed time the lock 300 may activate. The cell phone owners may be prevented from accessing their phone during the locked period. While in the cabinet, the one or more cell phones may be recharged and may be disinfected. At the end of the locked period, the lock 300 may deactivate and the one or more doors 260 may be opened.

Unless otherwise stated, the words "up", "down", "top", "bottom", "upper", and "lower" should be interpreted within a gravitational framework. "Down" is the direction that gravity would pull an object. "Up" is the opposite of "down". "Bottom" is the part of an object that is down farther than any other part of the object. "Top" is the part of an object that is up farther than any other part of the object. "Upper" refers to top and "lower" refers to the bottom. As a non-limiting example, the upper end of a vertical shaft is the top end of the vertical shaft.

As used in this disclosure, "AC" is an acronym for alternating current.

As used in this disclosure, an "application" or "app" is software that is specifically designed for use with a personal computing device.

As used herein, the words "couple", "couples", "coupled" or "coupling", refer to connecting, either directly or indirectly, and does not necessarily imply a mechanical connection.

As used in this disclosure, "DC" is an acronym for direct current.

As used in this disclosure, a "display" is a surface upon which is presented an image, potentially including, but not limited to, graphic images and text, that is interpretable by an individual viewing the image. When used as a verb, "display" is defined as presenting such an image.

As used in this disclosure, a "door" is a movable or removable barrier that is attached to the wall of a room or the surface of a container for the purpose of allowing or preventing access through an aperture into the room or container.

As used herein, "front" indicates the side of an object that is closest to a forward direction of travel under normal use of the object or the side or part of an object that normally presents itself to view or that is normally used first. "Rear" or "back' refers to the side that is opposite the front.

As used in this disclosure, a "handle" is an object by which a tool, object, or door is held or manipulated with the hand.

As used in this disclosure, "horizontal" is a directional term that refers to a direction that is perpendicular to the local force of gravity. Unless specifically noted in this disclosure, the horizontal direction is always perpendicular to the vertical direction.

As used in this disclosure, the word "interior" is used as a relational term that implies that an object is located or contained within the boundary of a structure or a space.

As used in this disclosure, "opaque" refers to an object or material that prevents the passage of radiation through the object or material.

As used in this disclosure, "translucent" refers to a material that allows light to pass through the material but that significantly scatters the light such that an object cannot be clearly seen through the material.

As used in this disclosure, "transparent" refers to a material that allows light to pass through the material without significant scattering such that an object can be clearly seen through the material.

As used in this disclosure, "UV" is an abbreviation for ultraviolet.

As used in this disclosure, "vertical" refers to a direction that is parallel to the local force of gravity. Unless specifically noted in this disclosure, the vertical direction is always perpendicular to horizontal.

With respect to the above description, it is to be realized that the optimum dimensional relationship for the various components of the invention described above and in FIGS. 1 through 4, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A modular cell phone storage locker comprising:
    a cabinet, one or more doors, one or more internal compartments, a lock, and a timer;
    wherein the modular cell phone storage locker provides a container where one or more cell phones are secured to prevent use of the one or more cell phones except during one or more predefined time periods;
    wherein the lock comprises an operator panel;
    wherein the operator panel comprises a key pad;
    wherein the operator panel is adapted to allow a cabinet administrator to control the operation of the lock by interacting with the key pad;
    wherein the operator panel comprises one or more indicators;
    wherein the one or more indicators express an operational state of the operator panel, the lock, the timer, or combinations thereof;
    wherein the lock comprises the timer;
    wherein the timer establishes the temporal boundaries of the one or more predefined time periods during which the one or more cell phones are or are not accessed;
    wherein during a locked period, the timer causes the lock to activate and prevent the one or more doors from opening;
    wherein during an unlocked period, the timer allows the lock to deactivate the lock and allow the one or more doors to be opened;
    wherein the one or more predefined time periods are defined using the key pad on the operator panel.

2. The modular cell phone storage locker according to claim 1
    wherein the cabinet comprises a rear wall, a left wall, a right wall, a top, and a bottom;
    wherein the cabinet is an enclosure for the modular cell phone storage locker;
    wherein the left edge of the rear wall is coupled to the rear edge of the left wall;
    wherein the right edge of the rear wall is coupled to the rear edge of the right wall;
    wherein the top edge of the rear wall is coupled to the rear edge of the top;
    wherein the bottom edge of the rear wall is coupled to the rear edge of the bottom;
    wherein the top edge of the left wall is coupled to the left edge of the top;
    wherein the bottom edge of the left wall is coupled to the left edge of the bottom;
    wherein the top edge of the right wall is coupled to the right edge of the top;
    wherein the bottom edge of the right wall is coupled to the right edge of the bottom.

3. The modular cell phone storage locker according to claim 2
    wherein the one or more doors are front covers for the cabinet;
    wherein each of the one or more doors are hingedly coupled to the cabinet via one or more door hinges;
    wherein the one or more doors are locked in a closed position to prevent access to the contents of the cabinet;
    wherein the one or more doors are moved to an open position when not locked to provide access to the contents of the cabinet.

4. The modular cell phone storage locker according to claim 3
    wherein each of the one or more doors comprise one or more viewing panes which are transparent or translucent;
    wherein the one or more viewing panes allow viewing of the contents of the cabinet.

5. The modular cell phone storage locker according to claim 4
    wherein the one or more viewing panes are UV opaque.

6. The modular cell phone storage locker according to claim 4
    wherein the cabinet comprises one or more internal dividers;
    wherein the rear wall, the left wall, the right wall, the top, the bottom, and the one or more doors comprise a grouping of walls referred to as external walls;
    wherein the external walls, the one or more internal dividers, or combinations thereof define the one or more internal compartments;
    wherein each of the one or more internal compartments is a storage location for an individual cell phone.

7. The modular cell phone storage locker according to claim 6
    wherein the one or more internal dividers comprise one or more internal horizontal dividers;
    wherein the one or more internal horizontal dividers are horizontal planes dividing the interior of the cabinet into two or more distinct, vertically-aligned spaces;
    wherein the one or more internal horizontal dividers are coupled at their rear edge to the rear wall, on their left edge to the left wall, and at their right edge to the right wall.

8. The modular cell phone storage locker according to claim 6
    wherein the one or more internal dividers comprise one or more internal vertical dividers;
    wherein the one or more internal vertical dividers are vertical planes dividing the interior of the cabinet into two or more distinct, horizontally-aligned spaces;
    wherein the one or more internal vertical dividers are coupled at their rear edge to the rear wall, on their top edge to the top, and at their bottom edge to the bottom.

9. The modular cell phone storage locker according to claim 6
wherein the one or more internal compartments are organized into rows where each of the one or more internal compartments in a row is the same height above the bottom, into columns where each of the one or more internal compartments in a column is the same distance from the left wall, or into a matrix of rows and columns.

10. The modular cell phone storage locker according to claim 9
wherein the lock is a device that prevents the one or more doors from opening when locked and allows the one or more doors to open when unlocked;
wherein the lock prevents opening when locked by creating an electromechanical linkage between the one or more doors, the cabinet, the one or more internal dividers, or combinations thereof;
wherein the lock allows opening by breaking the electromechanical linkage.

11. The modular cell phone storage locker according to claim 10
wherein the operator panel comprises a fingerprint reader;
wherein the fingerprint reader is adapted to allow the cabinet administrator to use a fingerprint to identify themselves to the lock.

12. The modular cell phone storage locker according to claim 11
wherein the modular cell phone storage locker comprises one or more time displays;
wherein the one or more time displays are mounted where they are visible from a position outside of the cabinet;
wherein the one or more time displays operate under the control of the timer and display time values pertinent to the operation of the timer.

13. The modular cell phone storage locker according to claim 12
wherein the one or more time displays display any or all of the current time, the time remaining until the lock is activated, the time remaining until the lock is deactivated, and/or the amount of time that the lock has been activated.

14. The modular cell phone storage locker according to claim 13
wherein the lock connects wirelessly to a software application installed on each of the individual cell phones that are placed inside of the cabinet;
wherein the software application on each of the individual cell phones disables or modifies features of the individual cell phones.

15. The modular cell phone storage locker according to claim 13
wherein the modular cell phone storage locker further comprises a charging port located within each of the one or more internal compartments;
wherein the charging port recharges the individual cell phone while the individual cell phone resides inside of one of the one or more internal compartments;
wherein the charging port comprises one or more power cables, one or more docking stations, or a combination thereof;
wherein the charging port is powered by AC power distributed within the cabinet to each of the one or more internal compartments from an AC power cord, by DC power distributed within the cabinet to each of the one or more internal compartments from a DC power supply, or by a combination thereof.

16. The modular cell phone storage locker according to claim 15
wherein the modular cell phone storage locker further comprises a disinfecting device located within each of the one or more internal compartments;
wherein the disinfecting device is a device that destroys bacteria on the surface of the individual cell phone.

17. The modular cell phone storage locker according to claim 16 wherein the disinfecting device is an ultraviolet (UV) light that is illuminated while the individual cell phone is within one of the one or more internal compartments.

18. The modular cell phone storage locker according to claim 17 wherein a solar panel is provided to generate electricity that is used in lieu of or in combination with the power cord in order to provide electricity for the charging port.

* * * * *